United States Patent [19]

Wojtowicz et al.

[11] 4,423,216

[45] Dec. 27, 1983

[54] PREPARATION OF CYANURIC ACID

[75] Inventors: John A. Wojtowicz, Cheshire; Haywood Hooks, West Haven, both of Conn.

[73] Assignee: Olin Corporation, New Haven, Conn.

[21] Appl. No.: 334,208

[22] Filed: Dec. 24, 1981

[51] Int. Cl.³ .......................................... C07D 251/32
[52] U.S. Cl. .................................................. 544/192
[58] Field of Search ........................................ 544/192

[56] References Cited

U.S. PATENT DOCUMENTS 3,164,591  1/1965  Walles et al. ...................... 260/248
3,635,968  1/1972  Goelz et al. .................... 260/248 A

*Primary Examiner*—John M. Ford
*Attorney, Agent, or Firm*—Arthur E. Oaks; Donald F. Clements

[57] ABSTRACT

A highly pure cyanuric acid is produced by a process which comprises gradually adding a nitrogenous material capable of producing cyanuric acid, such as urea, to a hot N-methylpyrrolidone solvent. The overall process converts substantially all of the urea to cyanuric acid which, upon drying, is a free flowing product capable of being converted into trichloroisocyanuric acid and similar compounds with a minimum of extra processing while allowing substantially complete recovery of the N-methylpyrrolidone solvent for reuse.

37 Claims, 3 Drawing Figures

PREPARATION OF CYANURIC ACID

BACKGROUND OF THE INVENTION

This invention relates to an improved method for making cyanuric acid from urea.

It is known that cyanuric acid can be produced by the pyrolysis of urea. This reaction may be expressed by the equation:

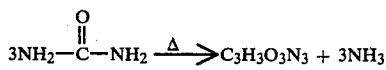

The resulting product, cyanuric acid, which has the empherical formula, $C_3H_3O_3N_3$, is generally expressed structurally either as:

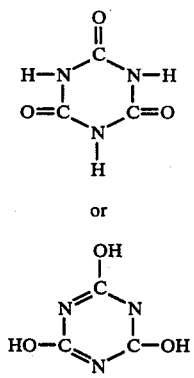

Pyrolysis can be carried out at temperatures above about 180° C. either in a dry state that is, in the absence of a solvent, as is described in U.S. Pat. No. 2,943,088 issued to R. H. Westfall on June 28, 1960 or in the presence of various high boiling inert solvents. One of these, N-methylpyrrolidone, is described in U.S. Pat. No. 3,164,591 issued to Wilhelm E. Walles et al on Jan. 5, 1965. However, when attempts are made to apply the method taught by Walles et al, it is found that cyanuric acid is obtained in only about a 60 to 70 percent yield. Moreover, the crude acid obtained contains substantial percentages of the mono- and diamides of cyanuric acid, commonly referred to as ammelide and ammeline as well as other undesirable side reaction products and "color bodies". Thus, the crude end product of this procedure is frequently not sufficiently pure to be readily converted into a number of chlorinated secondary products of commercial interest. To make it so, it must first be subjected to further processing for such purification. This normally includes a digestion of the crude cynauric acid in a strong acid medium, e.g., 3 to 15 percent sulfuric or hydrochloric acid to selectively hydrolyze the acid soluble cyanuric acid amides to convert them back to cynauric acid. In general, an acid digestion is required whenever the concentration of ammeline or ammelide exceeds about 2 percent by weight of the cyanuric acid product.

Still a further problem with the method of Walles et al is that of producing a free flowing product suitable for further processing.

It has been found that when the reaction mass is allowed to fall below a temperature of about 100° C., cyanuric acid and N-methylpyrrolidone combine to form an insoluble adduct which has a distinct tendency to "set up" into a hard concrete-like mass which must be broken up before any further use of the product can be made. Should this reaction occur during the processing steps used to remove the cyanuric acid from the reaction mass, such as filtering or centrifuging, drastic steps, sometimes involving disassembling the equipment and often damaging it, are necessary to remove the product and resume production.

It has also been found that even if the above adduct is broken up and then washed with water to remove residual solvent, it will often set up again into a concrete-like mass due to hydration of the cyanuric acid so that complete removal of the solvent to produce a purified product is difficult, if not impossible.

Lastly, the "color body" content is often sufficiently high that a supplemental bleaching operation is required to achieve a final product having a proper whiteness for commercial use.

SUMMARY OF THE INVENTION

It is an object of the present invention to provide a process that produces cyanuric acid product in a highly purified state, substantially free of cyanuric acid amides, so that acid digestion is not required.

It is a further object of the present invention to provide an improved process in which urea is converted essentially completely to produce a cyanuric acid product containing minimal amounts of color bodies and other impurities.

It is yet a further object of the present invention to describe a process which converts urea to cyanuric acid in high yields and in a form from which a free flowing cyanuric acid product can be readily recovered.

These and other objects of the subject invention will become apparent from the following description and the appended claims.

It has now been found that the foregoing objects can be accomplished in a process in which a nitrogenous material such as urea or biuret is selectively pyrolyzed to form a cyanuric acid product containing only minimal amounts of impurities and color bodies by the slow, controlled addition of said nitrogenous material to N-methylpyrrolidone heated to a temperature of at least 180° C. When performed in accordance with this invention, N-methylpyrrolidone readily dissolves the urea while only dissolving limited amounts of cyanuric acid. It is found that the acid formed can be readily recovered from the reaction mass in a free flowing form having minimal amounts of impurities which can then be easily and conveniently utilized in a variety of processes.

DESCRIPTION OF THE INVENTION

Figure 1:
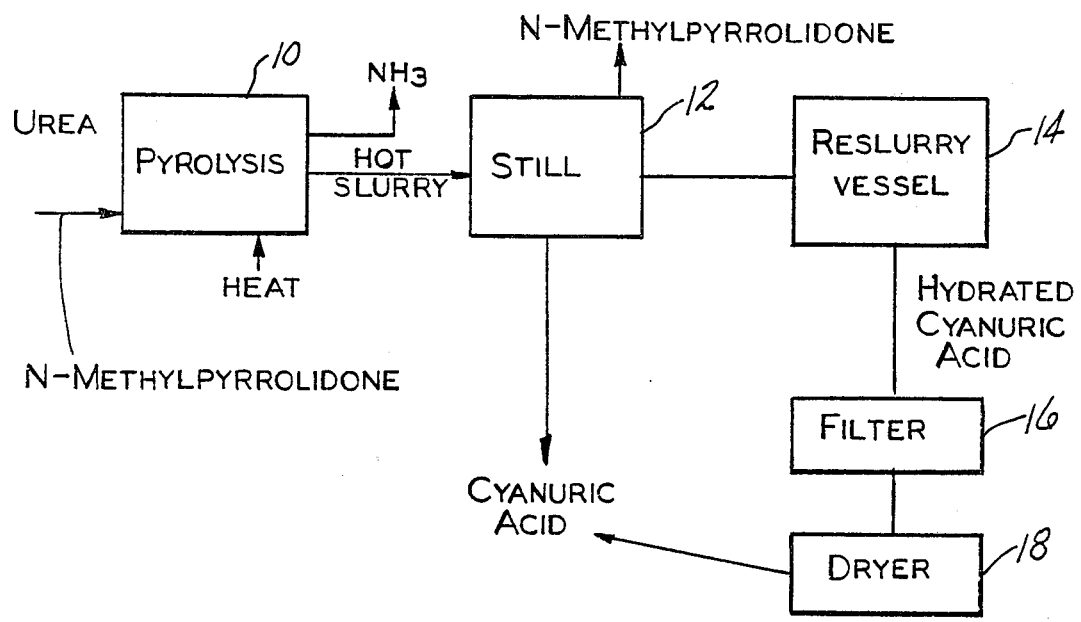
FIG. 1 is a flow diagram of a first embodiment of the subject invention, utilizing distillation to recover the cyanuric acid product.
Figure 2:
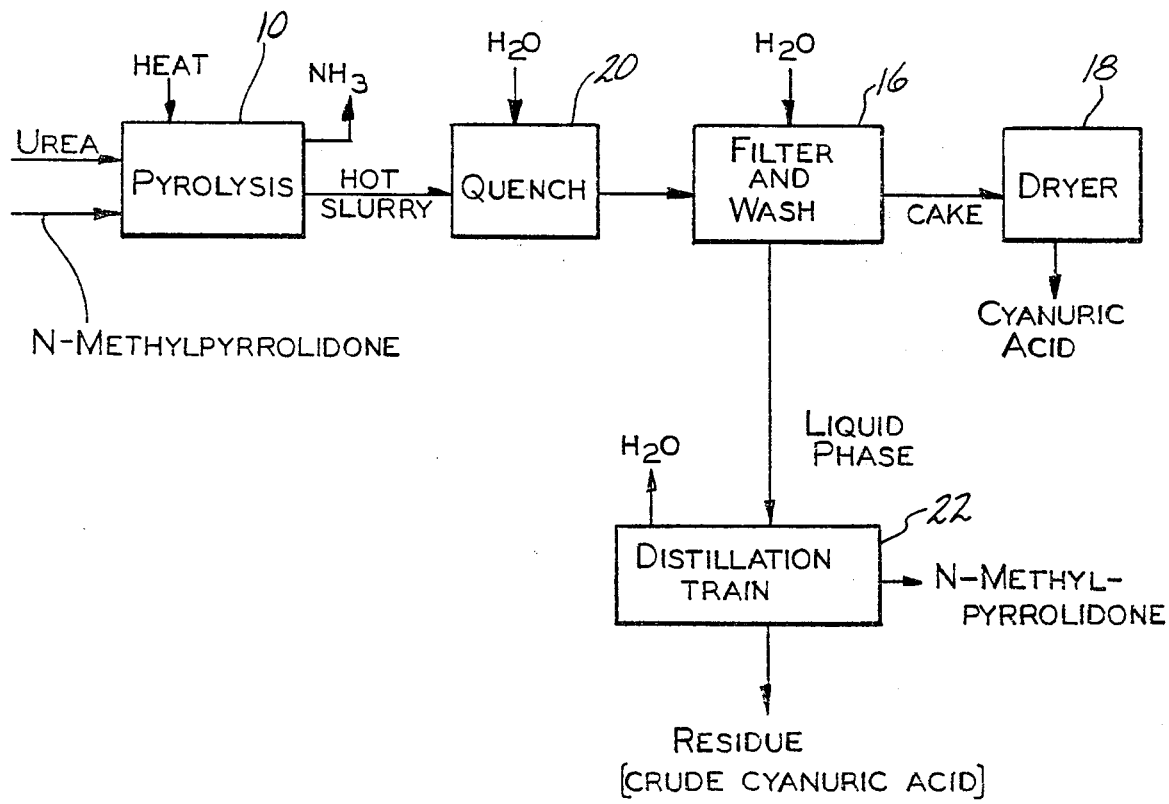
FIG. 2 is a flow diagram of a second embodiment of the subject invention, utilizing water quenching and filtration to recover the cyanuric acid product.
Figure 3:
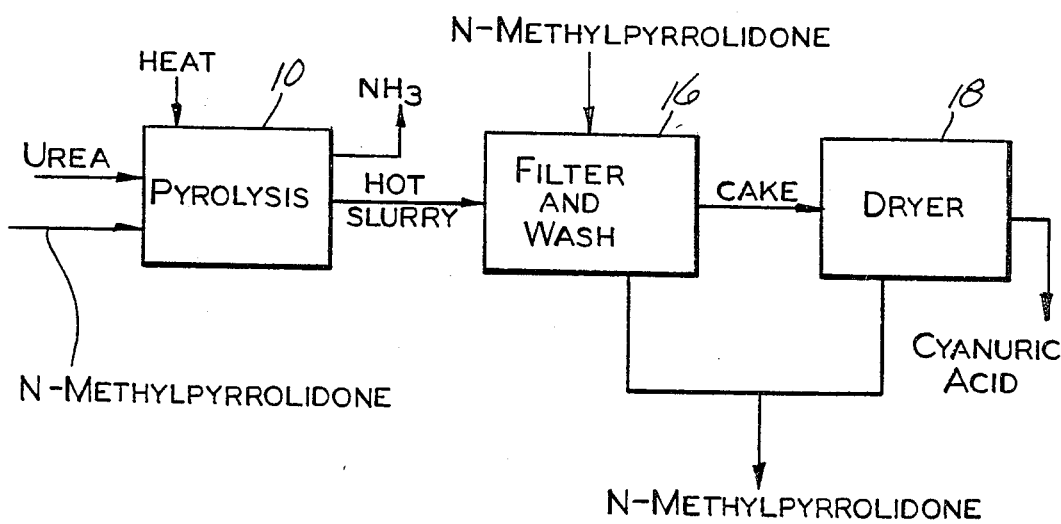
FIG. 3 is a flow diagram of a third embodiment of the subject invention, utilizing hot filtration to recover the cyanuric acid product.

FIGS. 1-3 show the basic method for producing and three different embodiments for recovering cyanuric acid from a reaction mass produced by pyrolyzing a nitrogenous product, such as urea or biuret, with urea being preferred, dissolved in a solvent. It has been shown that thermal condensation of urea to cyanuric acid can be carried out when urea is dissolved in a solvent of the general formula

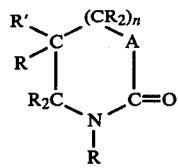

wherein R is hydrogen or a lower alkyl group containing 1-4 carbon atoms, R' is hydrogen, a lower alkyl group containing 1-4 carbon atoms, or phenyl, A is an oxygen atom or $CR_2$, R being defined as above, and n is 0 or 1 when A is oxygen and n is 0 when A is $CR_2$. The general formula shown therefore includes 2-pyrrolidones, 2-oxazolidones, and tetrahydro-1,3-oxazin-2-ones, all of which are revealed as being substantially substitutable for each other for urea pyrolysis. However, for reasons of availability and price, N-methylpyrrolidone is preferred.

In the process of this invention, as shown in these drawings, the urea is gradually added, preferably in the form of prills having a minimum of "fines" or other powdery material, or as a molten stream to a heated pyrolysis vessel 10 containing N-methylpyrrolidone. To provide a satisfactory reaction rate, this should be heated to a temperature of at least 180° C. and preferably to a temperature in the range of about 190° to 210° C. The urea charge is carefully controlled so as to provide a urea to solvent ratio of from about 0.5:1 to about 2:1 and preferably from about 0.9:1 to about 1.5:1. This should be done with a uniform addition rate of between about 0.1 and about 1.25 and preferably from between about 0.2 to about 0.8 pounds of urea/hour/pound of solvent. When the preferred rate of addition is used, it is found that the cyanuric acid product will contain less than 2% ammelide and ammeline impurities so that for most uses a supplementary acid digestion will not be required.

At the end of this addition, the reaction mass comprises a hot slurry of about 25 to about 60% and preferably from about 30 to about 50% by weight of cyanuric acid suspended in liquid N-methylpyrrolidone. As will be shown below, it is this controlled gradual addition of urea which produces the improved quality and yield of cyanuric acid end product achieved by the present invention.

The condensation reaction produced by pyrolysis is endothermic so that this rate of addition smooths out and simplifies the problem of providing the heat needed to start and maintain the condensation reaction. Further, by keeping the instantaneous concentration of urea low at all times, the condensation reaction forming the cyanuric acid tends to proceed quickly and smoothly with essentially all of the urea reacting and with a minimum of unwanted by-products being produced. In so doing, the formation and emission of $NH_3$ occurs at a relatively low but steady rate. Such a situation permits significant economies in the design and implementation of any units which might be used to recover this valuable by-product. Further, it is a significant factor in the reduction in the ammelide and ammeline content in the product of this reaction.

The pyrolysis and condensation reaction described above can be performed under either subatmospheric, atmospheric or superatmospheric pressure conditions. Each mode of operation offers particular advantages and disadvantages and the use of any of them is within the ambit of this invention. With subatmospheric pressure operation, the ease of removing or purging the by-product ammonia from the pyrolysis vessel is greatly enhanced due to a somewhat slower reaction rate. However, for practical purposes it is not desirable to go much below a 500-550 torr pressure since the boiling point of N-methylpyrrolidone will fall to below 180° C. At these conditions of temperature and pressure, the combined amount of ammelide or ammeline which is produced in the final reaction product is normally no greater than about 1 percent and is usually much less. Furthermore, the conversion of urea to cyanuric acid is substantially complete with total yields as high as 99 percent by weight or higher frequently being obtained.

Pyrolysis can also be performed at a higher pressure, such as 760 torr (1 atmosphere). While the reaction rate is faster and the final product tends to have a slightly higher level of ammelide or ammeline than with subatmospheric pressure operation, it has been found that the product obtained is quite satisfactory with essentially 100 percent urea conversion being obtained and no particular difficulty in recovering the by-product ammonia. Thus, an atmospheric pressure reaction, which requires no special facilities for producing and holding a vacuum is the preferred mode of operation for this invention. In superatmospheric (i.e. greater than 760 torr) operation, ammonia removal is less complete so that ammeline and ammelide impurity levels tend to be higher than with atmospheric operation; sometimes reaching a level where an acid hydrolysis operation is required to remove them.

Where the cyanuric acid is intended as feedstock for subsequent chlorination reactions to produce products such as sodium dichloroisocyanurate or trichloroisocyanuric acid, lower levels (i.e. about 1 percent or less) of ammelide and ammeline do not present a significant quality problem since this treatment causes them to eliminate the amine groups and replace them with carbonyl oxygen so that the same end product is made but with some $NCl_3$ also being given off as a by-product.

At the conclusion of the pyrolysis, the reaction mass of crude cyanuric acid suspended in the hot liquid N-methylpyrrolidone may be maintained under a purge of inert gas such as nitrogen or ammonia for a post-reaction time of from about 5 to about 30 minutes at temperature. Where quenching or filtration means are used to recover the cyanuric acid this will allow the final pyrolysis of any unreacted urea present after which the cyanuric acid suspensate can be separated easily from the reaction mass. It is important that the reaction mass not be allowed to cool below about 100° C. and preferably not below 120° C. to avoid any tendency to form a 1:1 cyanuric acid N-methylpyrrolidone adduct which will solidify or "set up" in the pyrolysis vessel if cooled much below this temperature. The final cyanuric acid product is generally at least 99 percent pure with the total amount of ammelide and ammeline being considerably less than 1 percent by weight. As is shown by the examples below, this is true regardless of the recovery method and whether the final product is free flowing or caked.

The recovery of the crude cyanuric acid from the reaction mass and its subsequent purification can be performed by a variety of methods. In one such method, illustrated in FIG. 1, the hot cyanuric acid slurry is directly distilled in still 12 to recover the N-methylpyrrolidone, giving a relatively pure cyanuric acid containing only minor amounts of other reaction products. With the normally low by-product content, it is usually quite practical to use the crude product directly as a feed for the production of chloroisocyanurates.

The product obtained by this procedure ranges in color from an off-white to a light tan. It has been found that the use of Hastelloy C as the material of construction for the reactor seems to provide a whiter product (but not a more efficient conversion) than either stainless steel or glass. Where a purer whiter colored cyanuric acid is needed, it can simply be obtained by slurrying the crude product in water vessel 14, to permit hydration, treating with a chlorinating agent ($Cl_2$, NaOCl, $Ca(OCl)_2$ or a chloroisocyanurate) to bleach any color bodies present, filtering in filter 16, and drying in dryer 18. If the crude cyanuric acid is only slightly off color, bleaching to an acceptable whiteness can be done by simply treating the crystalline product in the dry state with gaseous chlorine in a suitable vessel such as a fluidized bed or a rotary drum reactor. The ability to essentially completely remove such color bodies by such a simple operation is an unexpected and surprising result of the process of this invention. This is a matter of considerable importance where the product is tobe used for swimming pool and similar treatment. Here a minimum whiteness value of 65 is normally specified and, as shown in the Examples below, salvaging of off color material now becomes a relatively simple and low cost procedure as compared to prior art methods involving treating a slurried product.

FIG. 2 shows a second embodiment for recovering the cyanuric acid from the pyrolysis step. In this case, the reaction mass is cooled by feeding it to quench vessel 20 containing sufficient water at ambient temperature to cool the slurry to 60°–90° C. The wet slurry is then filtered in filter 16 with the separated filter cake being washed with an additional amount of water at 60°–80° C. to further remove any retained N-methylpyrrolidone and/or soluble impurities. The filtration and washing must be performed at above about 60° C. to prevent hydration of the cyanuric acid in the filter. It has been found, however, that if the product is stirred it is possible to reduce the cyanuric acid solubility losses in the solvent by cooling it down to a temperature of about 25° to about 30° C. before filtering. This appears to be due to impurities in the mother liquor which act to retard the hydration and set up of the cyanuric acid at this temperature. Care must be used when this is done since uncontrolled hydration will occur if the filter cake is washed with cold water. To avoid this, the filter cake should be reslurried in water to allow a controlled hydration and then refiltered.

The filter cake may go to a flash dryer to produce an anhydrous product or it may go to a trough cooler (a jacketed screw feeder) (not shown) where the residual water may be absorbed without having the cyanuric acid set up thus providing a free flowing hydrated cyanuric acid suitable for use in preparation of chloroisocyanurates. The filtrate is processed in a multistage distillation train to separate the water from the N-methyl-pyrrolidone and dissolved solids. The pot residue from distillation comprises primarily a residue of cyanuric acid crystals mixed with some small amount of "color bodies" or tars which must be removed before it can be used for chlorinated isocyanurate production.

To eliminate the need for reslurrying the filter cake to achieve hydration, the initial slurry in quench tank 20 can be treated with an amount of caustic soda solution up to about 0.1 mol NaOH/mol cyanuric acid to initiate a controlled hydration at this stage. When treated this way, the cyanuric acid hydrates completely in about 2–3 hours without "setting up". After hydration, the slurry is neutralized with a hydrochloric or sulfuric acid solution and then filtered, washed, and dried as described above.

FIG. 3 shows a third embodiment of the process of this invention. In this case, the hot reaction mass from pyrolysis vessel 10 is filtered in filter 16 and washed with distilled N-methylpyrrolidone to produce a crude cyanuric acid filter cake and an N-methylpyrrolidone filtrate. The filtrate can be distilled to recover a substantially pure N-methylpyrrolidone for reuse. However, ot is often found that the levels of N-methylsuccinimide and color bodies are sufficiently low for the recovered filtrate to be recycled directly without further treatment.

To avoid problems with setting up of the slurry during filtration, the temperature is maintained above 100° C. and preferably about 120° C. in the slurry hold tank and in the filter. The filter cake is vacuum dried in dryer 18 with the small amount of N-methylpyrrolidone still on the product being recovered.

Whichever of these procedures is used, with proper handling procedures total solvent recovery generally in the range of 97-99 percent or even higher can be obtained. Furthermore, reuse of the solvent for as many as five or even more additional pyrolysis reactions shows that essentially no buildup of N-methylsuccimide, the main decomposition product, occurs. This capability adds a significant economic advantage to this process.

The highly selective nature of the present process in producing a cyanuric acid product containing only minimum amounts of impurities is extremely important in commercial manufacture. The very low levels of amide impurities produced by slow addition of urea obviates the need for digesting the present cyanuric acid product in a strong mineral acid. Since this digestion step is a relatively long procedure, requiring several hours, and further since it requires special, acid resistant holding tanks and centrifuges to hold the acid and recover the digested cyanuric acid, the process of this invention provides still another marked advantage over many prior art processes by eliminating the need for this costly and time-consuming operation.

The following Examples are given to illustrate the invention and are not deemed to be limiting thereof. All parts and percentages are by weight unless otherwise specified.

EXAMPLES 1-4

A quantity of N-methylpyrrolidone solvent was charged into a 3-neck 1-liter glass flask fitted with a stirrer, thermometer, condenser, and urea addition funnel. The solvent was heated to reflux (about 202° C.) under an $NH_3$ purge flowing at a rate of about 500 cc/min. When reflux was achieved, urea was added intermittently, in small portions, over periods of time lasting from 0.55 to 3.5 hours. After an 0.5 hour post reaction hold time at temperature, the reaction mass was quenched in 400 ml of water. After cooling to room temperature, the resultant slurry was filtered and the filter cake washed with an additional 300 ml of water. On washing with water, the cyanuric acid hydrated, releasing some heat and forming a hardened mass which was broken up prior to drying. After drying, the crude cyanuric acid product was analyzed for amide impurities. The quantities of materials and rates of urea addition along with the results obtained are summarized in Table I.

TABLE I

Cyanuric Acid Purity As A Function Of Urea Addition Time

| Example | Urea Addition Time (hrs.) | Urea (gms.) | Solvent (gms.) | Grams of Urea Per Hour Per Gram of Solvent | Total Ammelide and Ammeline % |
|---|---|---|---|---|---|
| 1 | 0.55 | 169.8 | 266.4 | 1.15 | 2.34 |
| 2 | 0.90 | 270 | 360 | 0.83 | 2.22 |
| 3 | 1.02 | 270 | 360 | 0.73 | 1.92 |
| 4 | 3.5 | 335 | 375 | 0.26 | 0.46 |

EXAMPLES 5-9

375 g of N-methylpyrrolidone solvent was charged into a 1-liter, 316 stainless steel Parr Autoclave fitted with a stirrer, condenser, thermometer, and urea addition funnel. The assembled system was purged with $NH_3$ flowing at about 500 ml/min. while the solvent was heated to reflux (about 202° C.) by means of an oil bath. 335 g of urea prills were then added intermittently, in small portions, over a 3.5-hour period. At the conclusion of the reaction, the condenser was reoriented for distillation. About 80-85% of the N-methylpyrrolidone solvent distilled off at atmospheric pressure with the remaining solvent being removed under a reduced pressure in the range of 1 to 5 torr. About 240 g of crude cyanuric acid (approximately 100% yield) was obtained with the recovered solvent distillate was returned to the reactor for reuse. This procedure was followed in 5 consecutive test runs with the results shown in Table II. At the conclusion of the fifth run (Example 9), the solvent quality seemed unaffected and no significant buildup of N-methylsuccinimide or other decomposition products was observed.

tion after 16 hours, such a condition being achieved with complete dispersion of the cyanuric acid crystals in the still liquid water/N-methylpyrrolidone mixture. This slurry was filtered and washed 3 times with 100 ml of water. The wet crystals were dried to produce a 95% yield of anhydrous cyanuric acid containing 0.44% combined ammelide and ammeline.

The N-methylpyrrolidone was recovered from the filtrate by fractional distillation. Analysis of the pot residue remaining after distillation showed it to contain an additional 4% to 5% yield of cyanuric acid raising the total yield to over 99%.

EXAMPLE 11

The procedure of Example 10 was repeated but with the quenched reaction mass being filtered after it reached room temperature and the filter cake being reslurried in about 300 ml of water. When this was done, the cyanuric acid hydrated almost immediately. This slurry was filtered and the wet crystals dried to produce about a 92% yield of anhydrous cyanuric acid.

EXAMPLE 12

The procedure of Example 10 was repeated with the hot slurry being split into two portions. The first portion was quenched with the results of Example 10 being obtained, i.e. the slurried cyanuric acid being unhydrated after about 2 hours, but hydrating completely after 16 hours of additional stirring. The second portion,

TABLE II

Effect Of Solvent Recycle

| Example | Color | Whiteness | % Yield | CA | Ad & Am | $NH_3$ | Urea | Biuret | NMP & NMS |
|---|---|---|---|---|---|---|---|---|---|
| 5 | light tan | | 100.0 | 99.2 | 0.56 | 0.01 | 0.03 | <0.1 | 0.02 |
| 6 | light tan | | 100.0 | 99.3 | 0.49 | — | — | <0.1 | 0.10 |
| 7 | off-white | 37 | 100.0 | 99.3 | 0.43 | 0.02 | 0.02 | <0.1 | 0.12 |
| 8 | off-white | 47 | 100.0 | 99.5 | 0.43 | <0.01 | 0.01 | <0.1 | 0.06 |
| 9 | off-white | 46 | 99.2 | 99.4 | 0.40 | 0.01 | <0.01 | <0.1 | 0.07 |

CA = Cyanuric Acid
Ad = Ammelide
Am = Ammeline
NMP = N—methylpyrrolidone
MNS = N—methylsuccinimide

EXAMPLE 10

375 g of N-methylpyrrolidone solvent was charged into the apparatus of Examples 5-9 and heated as described therein. 335 g of urea prills were added in small portions over a 3.5-hour period at the conclusion of which the reaction mass was held at a temperature of between 200° and 210° C. for about 15 minutes. The hot slurry of crude cyanuric acid in solvent was then quenched with 485 g of water at about 25° C. This reduced the temperature of the total mass to between 80° and 90° C. from which point, under constant stirring, it cooled to room temperature. Observation showed no significant cyanuric acid hydration after about 2 hours of stirring but essentially complete hydrawhile still hot, was treated with about 7.5 g of 50% NaOH solution. This hydrated completely while being stirred over a 2.5-hour period.

EXAMPLE 13

The procedure of Example 10 was repeated with a 1-liter glass reactor and a nitrogen purge prior to the urea addition. After a two-hour stirring period, the crude cyanuric acid in the cooled slurry showed no sign of hydration at which time the slurry was vacuum filtered. The filter cake was then washed with water at which time the cyanuric acid hydrated. The hardened hydrated product was crushed and dried in an oven to produce a 93% yield of anhydrous cyanuric acid having an assay of 99+% purity and an ammelide content of 0.39% and an ammeline content of only 0.02%. Analysis of the filtrate showed an additional 6% yield of cyanuric acid.

EXAMPLE 14

The procedure of Example 13 was repeated but with a 1-liter, 316 stainless steel reactor and a 45-minute post reaction time before quenching. After cooling to about 50° C., 15 g of 50% NaOH solution was added to the stirred slurry, which resulted in the cyanuric acid hydrating over a period of about an hour. The caustic was neutralized with aqueous HCl prior to filtration. A 92% yield of dried cyanuric acid was obtained.

EXAMPLE 15

The procedure of Example 8 was repeated in a Hastelloy C reactor giving a cyanuric acid product having a whiteness of 62 as measured on a Photovolt Reflectance meter in which MgO has a whiteness value of 100. While commercial grade cyanuric acid has a whiteness value ranging from about 55 to 75 material designated for swimming pool use generally has a minimum value of 65.

EXAMPLE 16

Approximately 100 grams of the product of Example 15 after being crushed and screened to −50 mesh were placed in a stoppered 250 ml flask which was then filled with gaseous chlorine. After magnetically stirring for about 2-3 hours, the chlorine was purged with dry air. The cyanuric acid charge showed an increase in whiteness from a value of 62 to 69.

EXAMPLE 17

Using the method of Example 16, the product of Example 7 was treated with dry gaseous chlorine resulting in an increase in whiteness from 37 to 66.

EXAMPLE 18

The product from Example 8 was slurried in water and treated with gaseous chlorine. After filtration and drying, the product had a whiteness of 82.

The above examples show that the controlled gradual addition of urea to a heated N-methylpyrrolidone solvent produces essentially a quantitative conversion to a high purity cyanuric acid product which is readily adaptable to further processing. To distinguish the product and process of this invention from the prior art, Comparative Example A, which is the procedure disclosed by Walles et al as Example 1 of U.S. Pat. No. 3,164,591, supra, was performed.

COMPARATIVE EXAMPLE A 300 g of urea prills and 495 g of N-methylpyrrolidone were charged into a 1-liter glass reactor fitted with stirrer, condenser and thermometer. The reaction mixture was heated with a mantle and maintained at reflux for a 2-hour period during which the reaction temperature increased from 185° to 212° C. On cooling, the reaction mixture solidified at about 35° C. The reaction mixture was reheated to about 160° C. to make it stirrable, cooled to 40°-50° C. and filtered. The cake set up in the filter funnel and had to be broken up. On washing with water, the filter cake solidified again into a hard cement-like solid with release of some heat. The solid was broken up, washed further, and dried giving 129 g (60% yield) of impure cyanuric acid containing 5.6% ammelide and 0.4% ammeline.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. In a process for making cyanuric acid by pyrolyzing a nitrogenous material capable of yielding a cyanuric acid product, said material being dissolved in an N-methylpyrrolidone solvent in a pyrolysis vessel to produce a hot reaction mass comprising a slurry of crude cyanuric acid product suspended in said solvent, characterized by the improvements which comprise:
   a. adding said nitrogenous material to said pyrolysis vessel in a gradual controlled manner wherein the rate for said gradual addition is from about 0.1 to about 1.15 pounds of nitrogenous material/hour/pound of solvent; and
   b. maintaining said reaction mass at a temperature in excess of about 100° C. during recovery of said cyanuric acid from said reaction mass.

2. The process of claim 1 wherein said addition rate is from about 0.2 to about 0.8 pounds of nitrogenous material/hour/pound of solvent.

3. The process of claim 1 wherein nitrogenous material is added to said solvent sufficient to provide a solvent:cyanuric acid weight ratio of from about 0.5 to about 2.0 after pyrolysis is completed.

4. The process of claim 2 wherein said weight ratio is from about 0.9 to about 1.5.

5. The process of claim 1 wherein said nitrogenous bearing material is urea.

6. The process of claim 1 wherein said pyrolysis vessel is maintained at atmospheric pressure.

7. The process of claim 1 wherein said pyrolysis vessel is maintained below atmospheric pressure while said nitrogenous material is being added.

8. The process of claim 1 wherein the pressure within said pyrolysis vessel is from about 500 to about 550 torr.

9. The process of claim 1 wherein said solvent is heated to a temperature above about 180° C. before said nitrogenous material is added.

10. The process of claim 9 wherein said solvent is heated to a temperature in the range of about 190° C. to about 210° C.

11. The process of claim 1 further comprising the step of maintaining the heated reaction mass at the conclusion of the time for the addition of said nitrogenous material under a purge of an inert gas for a post-reaction time of from about 5 to about 30 minutes at the temperature of said pyrolysis.

12. The process of claim 1 further comprising the steps of removing said slurry from said pyrolysis vessel and separating a solid cyanuric acid product from said solvent and returning said solvent to said pyrolysis vessel.

13. The process of claim 12 wherein said cyanuric acid separation comprises distilling said slurry whereby said solvent is removed and recovered for reuse with said cyanuric acid remaining as a residue.

14. The process of claim 12 wherein said cyanuric acid separation comprises quenching said slurry in water so that it is cooled to a temperature in the range of from about 60° C. to about 90° C., filtering said quenched slurry to recover a crude cyanuric acid filter cake therefrom, and washing said filter cake with water at a temperature in the range of from about 60° C. to about 80° C. to remove residual solvent and soluble impurities.

15. The process of claim 14 wherein said quenched slurry is cooled to a temperature range of from about 25° C. to about 30° C. before filtration, said process further comprising reslurrying said filter cake in water so that controlled hydration of the cyanuric acid may occur and refiltering said reslurryed product to recover hydrated cyanuric acid therefrom.

16. The process of claim 14 wherein said quenched slurry is treated with sodium hydroxide solution up to an amount of about 0.1 mole NaOH per mole of cyanuric acid, stirred for a time of from about 2 to about 3 hours to induce controlled hydration and neutralizing said sodium hydroxide with an acid solution prior to filtering said slurry.

17. The process of claims 14, 15, or 16 wherein the filtrate from said filtered quenched slurry is distilled to remove the quench water and recover the solvent for reuse.

18. The process of claim 12 wherein cyanuric acid separation comprises filtering said hot reaction mass.

19. The process of claim 18 wherein said slurry is filtered at a temperature above about 120° C.

20. The process of claim 12 further comprising the step of bleaching said cyanuric acid product with a chlorinating agent selected from the group consisting of $Cl_2$, NaOCl, $Ca(OCl)_2$ and a chloroisocyanurate to remove said color bodies from said product.

21. The process of claim 20 wherein the bleaching step is performed with dry chlorine gas.

22. In a process for making cyanuric acid comprising heating a quantity of N-methylpyrrolidone solvent to a temperature sufficient to cause the pyrolysis and conversion of urea to cyanuric acid in a pyrolyzing vessel and maintaining said solvent at said temperature while adding urea thereto to form a hot reaction mass comprised of a slurry of cyanuric acid crystals in said solvent, the improvements comprising:
a. gradually adding to and dissolving said urea in said heated solvent, said urea quantity having a weight ratio to said solvent of between about 0.9:1 to about 1.5:1, the rate for said addition being between about 0.2 and about 0.8 pounds of urea/hour/pound of solvent, whereby said urea is pyrolyzed to produce a slurry of cyanuric acid in said reaction mass;
b. after adding said urea, maintaining the heated slurry at a temperature in excess of about 100° C. under a purge of an inert gas for a post-reaction time of from about 5 to about 30 minutes; and
c. distilling said hot reaction mass to separate said solvent from said cyanuric acid.

23. In a process for making cyanuric acid comprising heating a quantity of N-methylpyrrolidone solvent to a temperature sufficient to cause the pyrolysis and conversion of urea to cyanuric acid in a pyrolyzing vessel and maintaining said solvent at said temperature while adding urea thereto to form a hot reaction mass comprised of a slurry of cyanuric acid crystals in said solvent, the improvements comprising:
a. gradually adding to and dissolving said urea in said heated solvent, said urea quantity having a weight ratio to said solvent of between about 0.9:1 to about 1.5:1, the rate for said addition being between about 0.2 and about 0.8 pounds of urea/hour/pound of solvent, whereby said urea is pyrolyzed to produce a slurry of cyanuric acid in said reaction mass;
b. at the conclusion of the time for the adding said urea, maintaining the heated slurry at a temperature in excess of about 100° C. under a purge of an inert gas for a post-reaction time of from about 5 to about 30 minutes;
c. removing said hot reaction mass from said pyrolysis vessel and quenching it in water to a temperature of between about 60° C. and about 90° C.;
d. filtering said quenched reaction mass to separate said cyanuric acid from said slurry to form a filter cake and a solvent/water filtrate;
e. washing said filter cake with water having a temperature in the range of between about 60° C. to about 80° C. to remove soluble impurities;
f. distilling said filtrate to remove said water from said filtrate and recover said solvent for reuse; and
g. drying said filter cake to produce a free flowing cyanuric acid.

24. The process of claim 23 wherein said solvent is further distilled to provide a purified solvent as the distillate and a crude cyanuric acid product as a residue.

25. In a process for making cyanuric acid comprising heating a quantity of N-methylpyrrolidone solvent to a temperature sufficient to cause the pyrolysis and conversion of urea to cyanuric acid in a pyrolyzing vessel and maintaining said solvent at said temperature while adding urea thereto to form a hot reaction mass comprised of a slurry of cyanuric acid crystals in said solvent, the improvements comprising:
a. gradually adding to and dissolving said urea in said heated solvent, said urea quantity having a weight ratio to said solvent of between about 0.9:1 to about 1.5:1, the rate for said addition being between about 0.2 and about 0.8 pounds of urea/hour/pound of solvent, whereby said urea is pyrolyzed to produce a slurry of cyanuric acid in said reaction mass;
b. after adding said urea, maintaining the heated slurry at a temperature in excess of about 100° C. under a purge of an inert gas for a post-reaction time of from about 5 to about 30 minutes;
c. removing said hot reaction mass from said pyrolysis vessel and quenching it in water and cooling to a temperature in the range of between about 25° C. to about 30° C.;
d. filtering said quenched slurry to remove said cyanuric acid as a filter cake;
e. distilling the filtrate from said quenched slurry to remove said water from said filtrate and recover said solvent for reuse;
f. reslurrying said filter cake in water to allow a controlled hydration;
g. filtering said hydrated cyanuric acid from said reslurried filter cake; and
h. drying said hydrated cyanuric acid filter cake to produce a free flowing cyanuric acid.

26. In a process for making cyanuric acid comprising heating a quantity of N-methylpyrrolidone solvent to a temperature sufficient to cause the pyrolysis and conversion of urea to cyanuric acid in a pyrolyzing vessel and maintaining said solvent at said temperature while adding urea thereto to form a hot reaction mass comprised of a slurry of cyanuric acid crystals in said solvent, the improvements comprising:

a. gradually adding to and dissolving said urea in said heated solvent, said urea quantity having a weight ratio to said solvent of between about 0.9:1 to about 1.5:1, the rate for said addition being between about 0.2 and about 0.8 pounds of urea/hour/pound of solvent, whereby said urea is pyrolyzed to produce a slurry of cyanuric acid in said reaction mass;

b. at the conclusion of the time for the adding said urea, maintaining the heated slurry at a temperature in excess of about 100° C. under a purge of an inert gas for a post-reaction time of from about 5 to about 30 minutes;

c. removing said hot reaction mass from said pyrolysis vessel and quenching it in water to a temperature of between about 60° C. and about 90° C.;

d. adding sodium hydroxide solution to said slurry up to an amount of about 0.1 mole per mole of cyanuric acid and stirring the mixture for about 2 to about 3 hours to induce a controlled hydration;

e. neutralizing said sodium hydroxide with an acid solution;

f. filtering said neutralized slurry to recover a hydrated cyanuric acid filter cake; and g. drying said hydrated cyanuric acid filter cake to produce a free flowing cyanuric acid.

27. In a process for making cyanuric acid comprising heating a quantity of N-methylpyrrolidone solvent to a temperature sufficient to cause the pyrolysis and conversion of urea to cyanuric acid in a pyrolyzing vessel and maintaining said solvent at said temperature while adding urea thereto to form a hot reaction mass comprised of a slurry of cyanuric acid cyrstals in said solvent, the improvements comprising:

a. gradually adding to and dissolving said urea in said heated solvent, said urea quantity having a weight ratio of said solvent of between about 0.9:1 to about 1.5:1, the rate for said addition being between about 0.2 and about 0.8 pounds of urea/hour/pound of solvent, whereby said urea is pyrolyzed to produce a slurry of cyanuric acid in said reaction mass;

b. after adding said urea, maintaining the heated slurry at a temperature in excess of about 100° C. under a purge of an inert gas for a post-reaction time of from about 5 to about 30 minutes;

c. filtering said slurry to recover said cyanuric acid as a filter cake and a solvent filtrate; and d. drying said filter cake to produce a free flowing cyanuric acid.

28. The process of claims 22, 23, 25, 26 or 27 further comprising the step of bleaching said cyanuric acid product with a chlorinating agent selected from the group consisting of $Cl_2$, NaOCl, $Ca(OCl)_2$ and a chloroisocyanurate to remove said color bodies in said product.

29. The process of claim 28 wherein said bleaching step is performed with chlorine gas.

30. In a process for making cyanuric acid by pyrolyzing a nitrogenous material capable of yielding a cyanuric acid product, said material being dissolved in an N-methylpyrrolidone solvent in a pyrolysis vessel to produce a hot reaction mass comprising a slurry of crude cyanuric acid product suspended in said solvent, characterized by the improvements which comprise:

a. adding said nitrogenous material to said pyrolysis vessel in a gradual controlled manner wherein the rate for said gradual addition is from about 0.1 to about 1.15 pounds of nitrogenous material/hour/pound of solvent;

b. maintaining said reaction mass at a temperature in excess of about 100° C. during recovery of said cyanuric acid from said reaction mass; and c. bleaching said recovered cyanuric acid with a chlorinating agent selected from the group consisting of $Cl_2$, NaOCl, $Ca(OCl)_2$ and a chloroisocyanurate for a time sufficient to remove any color bodies present.

31. The process of claim 20 wherein said bleaching step is performed by admixing said chlorinating agent with a water slurry of said cynauric acid product.

32. The process of claim 21 wherein said $Cl_2$ is dry mixed with said solid cyanuric acid product.

33. The process of claim 28 wherein said bleaching step is performed by admixing said chlorinating agent with a water slurry of said cyanuric acid product.

34. The process of claim 29 wherein said $Cl_2$ is dry mixed with said solid cyanuric acid product.

35. The process of claim 30 wherein said bleaching step is performed by admixing said chlorinating agent with a water slurry of said cyanuric acid product.

36. The process of claim 30 wherein said bleaching step is performed with chlorine gas.

37. The process of claim 36 wherein said $Cl_2$ is dry mixed with said solid cyanuric acid product.

* * * * *